United States Patent [19]
Welsh

[11] 4,173,798
[45] Nov. 13, 1979

[54] INTRA-OCULAR LENS

[76] Inventor: Robert C. Welsh, 168 SE. First St., Miami, Fla. 33131

[21] Appl. No.: 902,830

[22] Filed: May 4, 1978

[51] Int. Cl.² ............................ A61F 1/16; A61F 1/24
[52] U.S. Cl. .......................................................... 3/13
[58] Field of Search .......................................... 3/13, 1

[56] References Cited

U.S. PATENT DOCUMENTS

| 4,092,743 | 6/1978 | Kelman | 3/13 |
| 4,113,088 | 9/1978 | Binkhorst | 3/13 X |

OTHER PUBLICATIONS

"Artiphakia and Aniseikonia" by Richard C. Troutman, American Journal of Ophthalmology, vol. 56, No. 2, Oct. 1963, pp. 602–639.

"History of Intraocular Implants" by D. P. Choyce, Annals of Ophthalmology, Oct. 1973, pp. 1113–1120.

"A Weightless Iseikonic Intraocular Lens" by Richard D. Binkhorst et al., American Journal of Ophthalmology, vol. 58, No. 1, Jul. 1964, pp. 73–78.

Primary Examiner—Ronald L. Frinks
Attorney, Agent, or Firm—Stevens, Davis, Miller & Mosher

[57] ABSTRACT

An improved iris plane intra-ocular lens for implantations into an aphakic human eye wherein the back side of the haptic crotch regions of each of the horizontal haptics is substantially chamfered for substantially decreasing warping of the iris at the pupillary margin.

5 Claims, 10 Drawing Figures

4,173,798

INTRA-OCULAR LENS

BACKGROUND

The present invention is an improvement in intraocular lenses for implantation into the human eye, replacing a cataractus natural lens. More specifically the present invention is an iris-plane intra-ocular lens which overcomes the problem of severe warping (sometimes called "basket-weaving") of the iris at the pupillary margin.

The problem of restoring useful vision to a human eye whose cataractus natural lens has been removed, i.e., an aphakic eye, has been with us for as long as cataract surgery has been performed. Various solutions for restoring aphakic vision have been attempted, and such solutions have included bulky thick spectacle lenses and contact lenses. Another solution has been the intra-ocular implantation of a manmade lens to replace the removed natural lens. A variety of such intra-ocular lenses have been used with various degrees of success and failure. Among known intra-ocular lenses are the Choyce lens, the Binkhorst 4-Loop Intra-Capsular lens, the Medallion Intra-Capsular lens, the 2-Loop Binkhorst Extra-Capsular lens, the 2-Loop Binkhorst with Iris Clip Extra-Capsular lens, the 4-Loop Binkhorst Maltese Cross lens, the Copeland and New Copeland lenses, the Federov Russian lens, and the new Posterior Chamber lens.

Iris plane intra-ocular lenses such as the Copeland lens have been known for some time, but they still cause severe warping or basket-weaving of the iris at the pupillary margin when implanted in the human eye. Such severe warping in turn often causes post-implant complications such as iritis, cystoid macular edema, and unnecessary glare.

BRIEF SUMMARY OF THE INVENTION

It is an object of the present invention to overcome the above-noted defects of prior intra-ocular lenses.

It is an object of the present invention to provide an intra-ocular lens which when implanted in the human eye does not create severe warping or basket weaving of the iris at the pupilary margin.

The present invention achieves the foregoing objects and others through an intra-ocular lens comprising a central lens area from which four haptics extend, two vertical haptics extending upwardly and downwardly, respectively from the central lens area, those vertical haptics designed to sit behind the iris when the lens is implanted in a human eye, and two horizontal haptics extending horizontally outwardly from the left and right of the central lens area, those horizontal haptics designed to sit in front of the iris and behind the cornea when the lens is implanted in a human eye, the junction region among two adjacent haptics and the central lens area being a haptic crotch, the back side of the lens being substantially flat, but the back side of the haptic crotch regions of each of the horizontal haptics being substantially chamfered for substantially decreasing warping of the iris at the pupillary margin.

BRIEF DESCRIPTION OF THE DRAWINGS

Other objects and further features of preferred embodiments of the present invention are shown in the accompanying drawings thereof, wherein.

DETAILED DESCRIPTION

Figure 1:
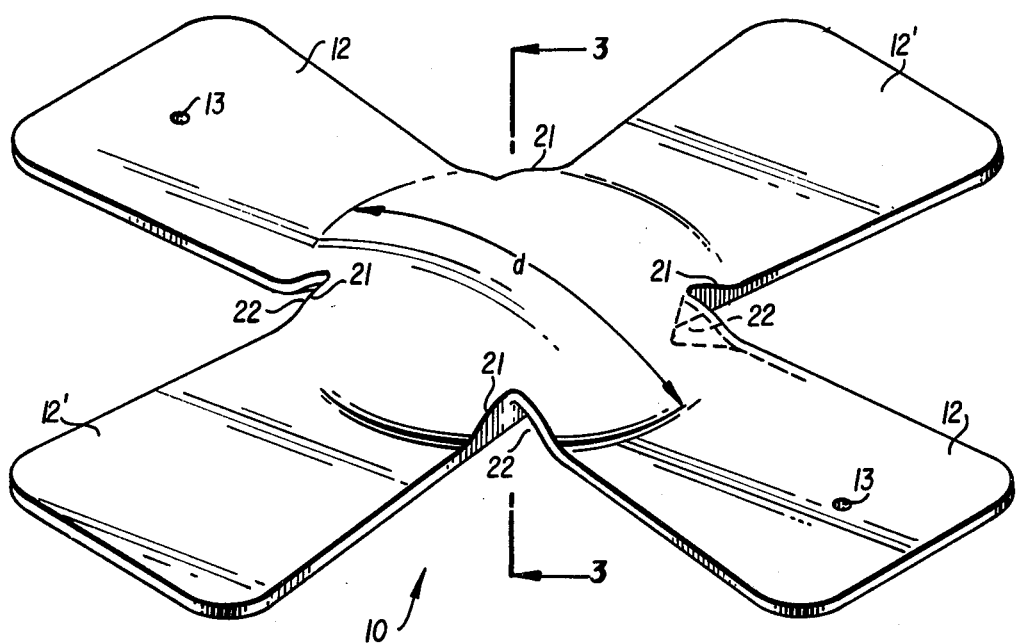
FIG. 1 is a partially schematic, isometric view of the front side of the advantageous intra-ocular lens of the present invention.
Figure 2:
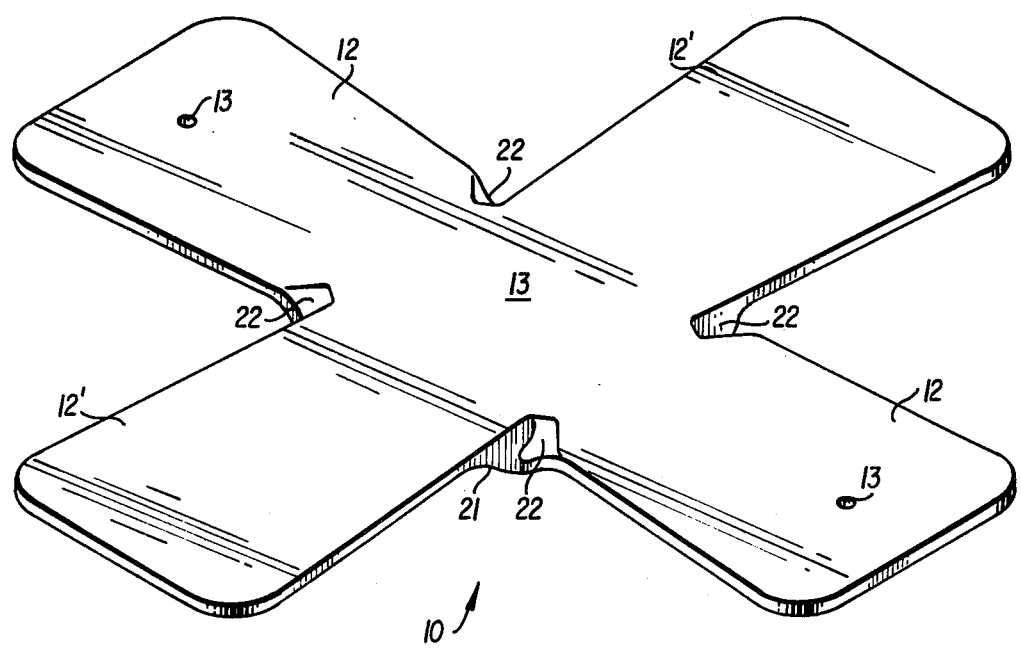
FIG. 2 is a partially schematic, isometric view of the back side of the lens of FIG. 1.
Figure 3:
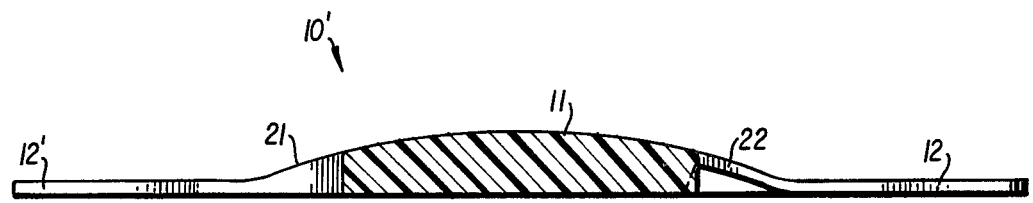
FIG. 3 is a partially schematic, cross-sectional view taken along lines III—III of FIGS. 1 and 2.

The advantageous iris plane intra-ocular lens of the present invention is illustrated in isometric front side and back side views, respectively, in FIGS. 1 and 2. The lens 10 generally comprises a central optic lens region 11 which could be thought of as a hub from which haptics 12, 12' extend like spokes of a wheel. As shown in FIG. 2, the back surface 13 of the lens is substantially flat, i.e. planar. The front surface of the lens in the central optic region 11 has a three-dimensionally curved surface as shown in FIG. 1. The surface of central optic lens region 11 covers a circular portion of the intra-ocular lens, and its front surface is typically spherical, as shown in FIG. 3. While the circular area of the optic region 11 may be of any suitable size, it is usually about 3.8 to 4.2 millimeters in diameter d, and the optic lens itself usually has power of about +8.00 to +30.00 diopters.

The intra-ocular lens of the present invention is designed so that when implanted in an human eye (as perhaps best shown in FIG. 6) the two haptics having optional holes 13 therein are oriented horizontally and hence called the horizontal haptics 12. The other two haptics 12' are designed to be oriented vertically and hence are called the vertical haptics 12'.

The intra-ocular lens of the present invention can be made of any suitable material which is inert and benign to the intra-ocular environment. Plastic materials such as polymethyl methacrylate, for example are suitable for this purpose.

Figure 4:
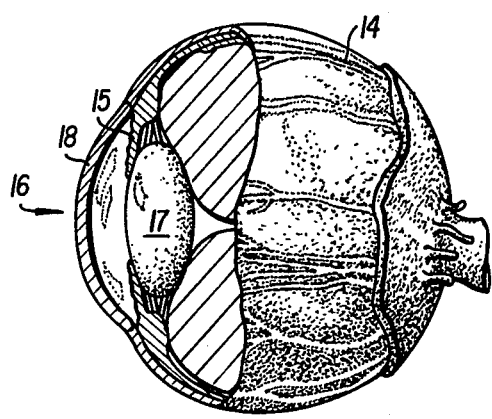
FIG. 4 is a partially schematic, cross-sectional view of an human eye.

FIG. 4 shows in partially schematic cross section the parts of the natural human eye which are directly involved with implantation of intra-ocular lenses. The eyeball generally is designated 14 and the normally visible portions of the eye include the colored iris 15 the central opening in which is the pupil 16. The edge of the colored iris which forms the pupil opening is known as the pupillary margin. Behind the pupil opening of the iris is the natural lens 17 which focuses incoming light on the retina at the internal rear of the eyeball. Overlying the iris, pupil and lens is a clear layer of tissue called the cornea 18. The cornea is the external protective layer for the eye; it also contributes about ⅔ of the optical power for focusing incoming light on the retina. The lens 17 completes the focusing job which is commenced by the cornea.

Figure 5:
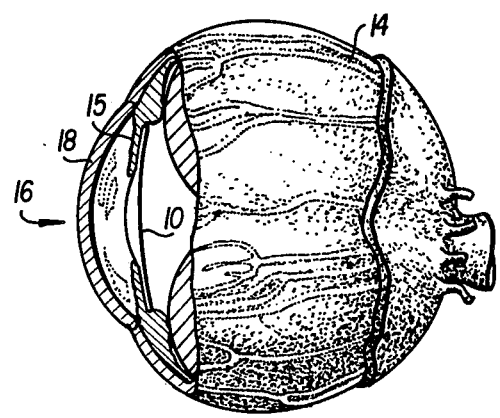
FIG. 5 is a partially schematic, cross-sectional view of an human eye including the implanted intra-ocular lens of the present invention.
Figure 6:
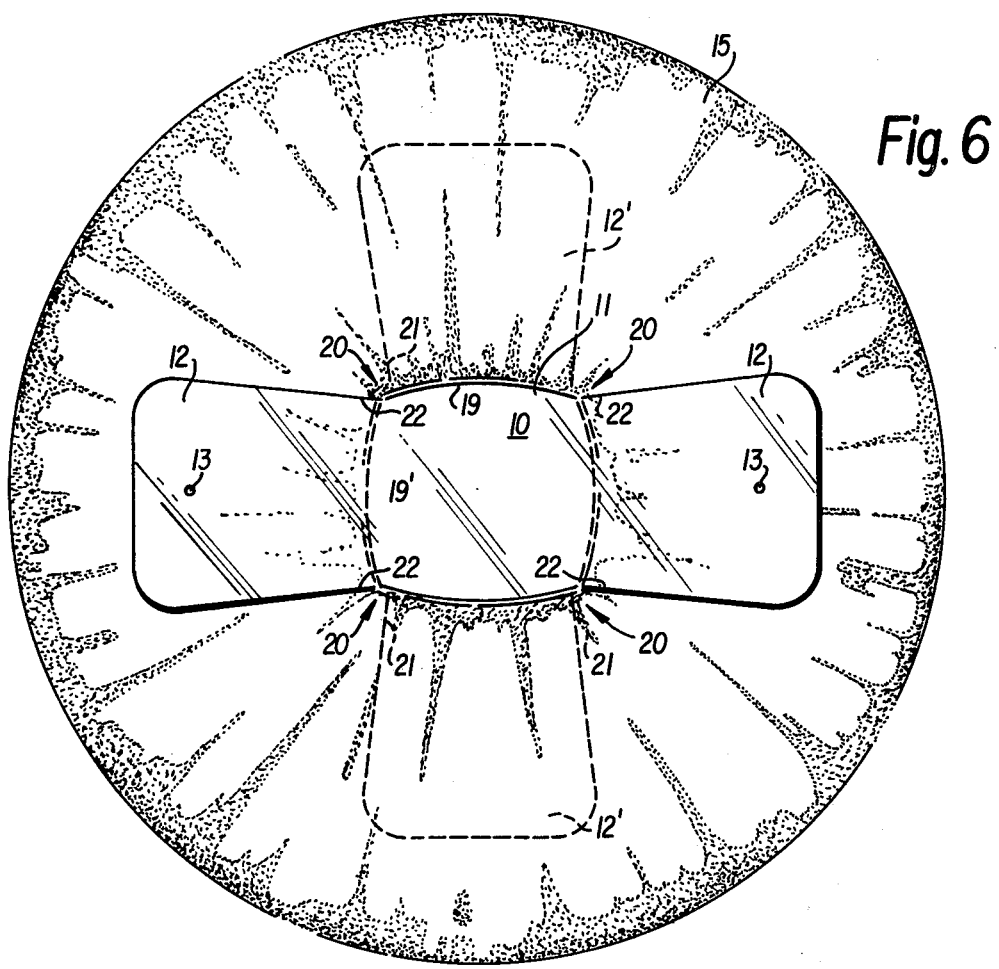
FIG. 6 is a partially schematic, front view of the iris and pupil portions of an human eye including the implanted intra-ocular lens of the present invention.

When the natural lens 17 becomes grossly cataractus, it may be surgically removed, and the iris plane intra-ocular lens of the present invention is designed to be implanted in place of the natural lens, as illustrated in FIGS. 5 and 6.

FIG. 6 is a partially schematic view of the iris portion of an eye in which the lens of the present invention has been implanted. As shown therein the vertical haptics 12' are inserted behind the iris 15. The iris sphincter, which controls the size of the pupil by increasing or decreasing the circumference of the pupillary margin 19, extends in front of the vertical haptics and within the circumference of the central optic region 11 of intra-ocular lens 10. The horizontal haptics lie in front of the iris 15 and behind the cornea which is not shown in FIG. 6. The pupillary margin passes behind the horizontal haptics as indicated by broken lines 19', also within the circumference of the central optic region 11. The curved optical front surface of the lens is of course highly polished, and the entire posterior planar surface of the lens is likewise polished to a very smooth optical quality finish. The edges of the haptics are also well polished to aid the iris and its pupillary margin in smoothly increasing and decreasing its circumference during normal dilation and contraction of the pupil.

Figure 7A:
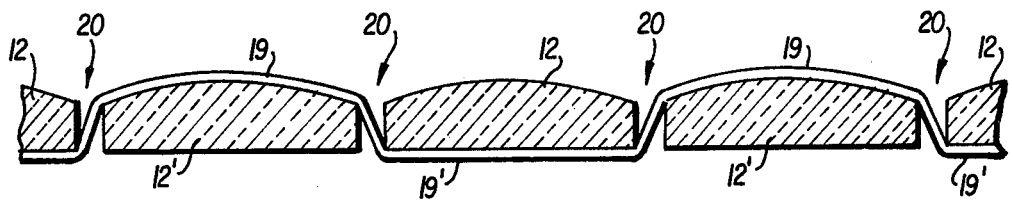
FIG. 7A is a schematic drawing showing in one plane the severely warped or basket-woven path of the pupillary margin through the haptics of the old iris plane lens.
Figure 7:
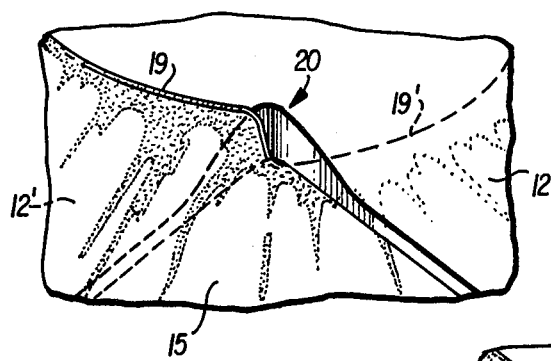
FIG. 7 is a partially schematic, cutaway isometric view showing the severely warped path of the pupillary margin through a haptic crotch in the old iris plane lens.

The troublesome portions of similar prior art iris plane intra-ocular lenses have been the haptic crotches indicated by arrows 20 in FIG. 6. The problem of severe iris warping or basket-weaving is illustrated in FIGS. 7 and 7A. FIG. 7 shows that the pupillary margin 19 of iris 15 must go through a tortuous path as it passes from in front of the anterior surface of vertical haptic 12' to behind the posterior surface of horizontal haptic 12. This sharp distortion of the iris at the pupillary margin is called severe warping or basket-weaving of the iris. This severe warping of the pupillary margin is schematically illustrated in planar form in FIG. 7A wherein cross-sections of the vertical haptics 12' and the horizontal haptics 12 are shown with a schematic representation of pupillary margin 19, extending in the plane of the paper upon which the drawing appears, as if the circumference of the pupillary margin were linear instead of circular. The spaces between adjacent haptics represent the haptic crotches 20 and the sharp distortion of the pupillary margin 19 as it passes through each haptic crotch 20 is self evident. This sharp distortion unnaturally extends the pupillary margin and iris sphincter, and that unnatural extension over the sharp corners of the posterior of the horizontal haptics contributes to iritis, cystoid macular edema and unnecessary aphakic glare.

In the advantageous lens of the present invention the surfaces of the haptics are modified in the haptic crotches to minimize warping of the iris and pupillary margin. As shown in FIG. 8, as well as in FIGS. 1–3 and 6, the anterior edges 21 of the vertical haptics 12' are rounded in the haptic crotches, and the posterior edges of the horizontal haptics 12 are chamfered at 22 in the haptic crotches. The rounded anterior edges and chamfered posterior edges, over which the pupillary margin of the iris must pass, greatly decrease the severity of the basket weaving of the pupillary margin, and thereby decrease adverse physiological and optical effects of intra-ocular lenses.

Figure 8A:
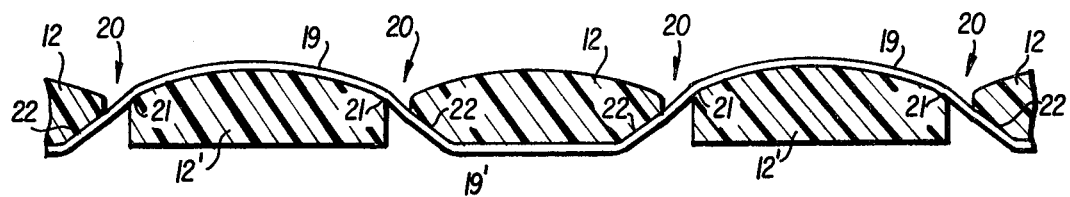
FIG. 8A is a schematic drawing showing in one plane the minimally warped path of the pupillary margin through the haptics of the advantageous intra-ocular lens of the present invention.
Figure 8:
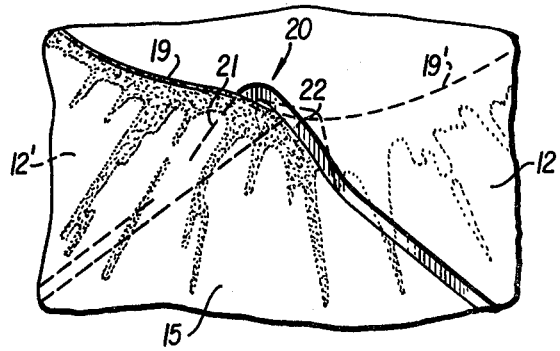
FIG. 8 is a partially schematic, cutaway isometric view showing the greatly improved, minimally warped path of the pupillary margin through a haptic crotch in the advantageous intra-ocular lens of the present invention.

As schematically illustrated in FIG. 8A (which is comparable to FIG. 7A of the prior art) the improvements of the present invention substantially decrease the extent of unnatural extension of the pupillary margin 19, and eliminate the very sharp corners over which the pupillary margin of the iris necessarily passed in prior intra-ocular lenses. This combination of decreased stress in the pupillary margin and iris sphincter, along with elimination of the potentially damaging sharp corners of the haptics over which the iris passes in the haptic crotches, provides outstanding improvements in the physiology and vision of an aphakic human eye into which the inventive intra-ocular lens has been implanted.

The iris plane intra-ocular lens of the present invention is designed for implantation into the human eye at the time a cataractus natural lens is removed from the human eye, or at any time months or years after removal thereof, an object of this invention being to restore normal and clear aphakic vision after surgical cataract removal from the eye. By substantially decreasing or minimizing the warping of the iris at the pupillary margin, the present invention also decreases post-implantation complications such as iritis, cystoid macular edema, and decreases glare in the lens. The lens is also relatively easily implanted by competent surgeons. For example it can be cartwheeled in thru a 6 mm. incision closed system.

Although specific components, proportions and arrangements of elements have been stated in the above description of preferred embodiments of this invention, other equivalent components and arrangement of elements may be used with satisfactory results and various degrees of quality, or other modifications may be made herein to enhance the construction of the invention to thereby increase its utility. It will be understood that such changes of details, materials, arrangements of parts, and uses of the invention described and illustrated herein, are intended to be included within the principles and scope of the claimed invention.

What is claimed is:

1. An iris plane intra-ocular lens for implantation into an aphakic human eye, comprising:
    a central lens area from which four haptics extend generally along two perpendicular lines, two of said haptics being vertical haptics extending upwardly and downwardly, respectively, from said central lens area, and the other two haptics extending horizontally from the sides of said central lens area, said vertical haptics for sitting behind the iris of an aphakic human eye into which the lens is implanted and said horizontal haptics for sitting in front of said iris but behind the cornea of said eye,
    each junction region among each two adjacent haptics and the central lens area being a haptic crotch, the posterior side of the lens being substantially flat, with the posterior side of each edge of the horizontal haptics being substantially chamfered in each haptic crotch, for minimizing warping of the iris of said eye at its pupillary margin.

2. The lens of claim 1, wherein the anterior edges of each vertical haptic are substantially rounded in each haptic crotch.

3. The lens of claim 1, wherein said central lens area is about 3.8 to about 4.2 millimeters in diameter.

4. The lens of claim 3, wherein said central lens area of the anterior surface of the lens is spherical in shape and has a power of about +8.00 to about +30.00 diopters.

5. The lens of claim 1, wherein said lens comprises polymethyl methacrylate.

* * * * *